US00PP29666P2

(12) United States Plant Patent
Elstgeest

(10) Patent No.: US PP29,666 P2
(45) Date of Patent: Sep. 11, 2018

(54) ***DIEFFENBACHIA* PLANT NAMED 'REEVA'**

(50) Latin Name: *Dieffenbachia amoena*
Varietal Denomination: REEVA

(71) Applicant: Elstgeest Youngplants, Rijsenhout (NL)

(72) Inventor: Debbie Elstgeest, Rijsenhout (NL)

(73) Assignee: Elstgeest Youngplants, Rijsenhout (NL)

( * ) Notice: Subject to any disclaimer, the term of this patent is extended or adjusted under 35 U.S.C. 154(b) by 0 days.

(21) Appl. No.: 15/732,273

(22) Filed: Oct. 17, 2017

(51) Int. Cl.
*A01H 5/12* (2018.01)

(52) U.S. Cl.
USPC ..... Plt./378
CPC ..... *A01H 5/12* (2013.01)

(58) Field of Classification Search
USPC ..... Plt./378
CPC ..... A01H 5/12; A01H 5/02; A01H 5/00
See application file for complete search history.

*Primary Examiner* — Kent L Bell
(74) *Attorney, Agent, or Firm* — Samuel R. McCoy, Jr.

(57) ABSTRACT

'REEVA' is a new and distinctive variety of *Dieffenbachia* which is characterized by a compact growth habit with numerous freely-branching main shoots, improved plant vigor, a relative abundance of large obovate foliage which is centrally and irregularly blotched light yellow-green, and the stability of all characteristics from generation to generation.

2 Drawing Sheets

Latin name of the genus and species: The Latin name of the genus and species of the novel variety disclosed herein is *Dieffenbachia amoena.*

Variety denomination: The inventive variety of *Dieffenbachia* disclosed herein has been given the variety denomination 'REEVA'.

BACKGROUND OF THE INVENTION

Parentage: 'REEVA' originated as a naturally-occurring, whole plant mutation of *Dieffenbachia amoena* 'Tropic Snow' (U.S. Plant Pat. No. 2,869). In August of 2012 the inventor discovered the mutation at a commercial greenhouse in Rijsenhout, The Netherlands, growing amongst a crop of *Dieffenbachia* 'Tropic Snow'. The mutation was noted for its freely-branching, compact growth habit and was subsequently isolated for further evaluation in order to confirm the distinctness and stability of the characteristics first observed. Upon confirmation of distinctness and stability, the new *Dieffenbachia* plant was selected for commercialization and given the name 'REEVA'.

Asexual Reproduction: Asexual reproduction of 'REEVA', by way of softwood stem cuttings, was first performed in the August of 2012 at a commercial greenhouse in Rijsenhout, The Netherlands. Five successive generations so produced have shown that the unique features of the instant cultivar are stable and reproduced true to type.

SUMMARY OF THE INVENTION

The cultivar 'REEVA' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Dieffenbachia* cultivar 'REEVA'. These traits, in combination, distinguish 'REEVA' as a new and distinct cultivar.

1. *Dieffenbachia* 'REEVA' exhibits a compact growth habit with numerous freely-branching main shoots; and
2. *Dieffenbachia* 'REEVA' exhibits improved plant vigor; and
3. *Dieffenbachia* 'REEVA' exhibits a relative abundance of large obovate foliage which is centrally and irregularly blotched light yellow-green.

BOTANICAL DESCRIPTION OF THE PLANT

Figure 1:
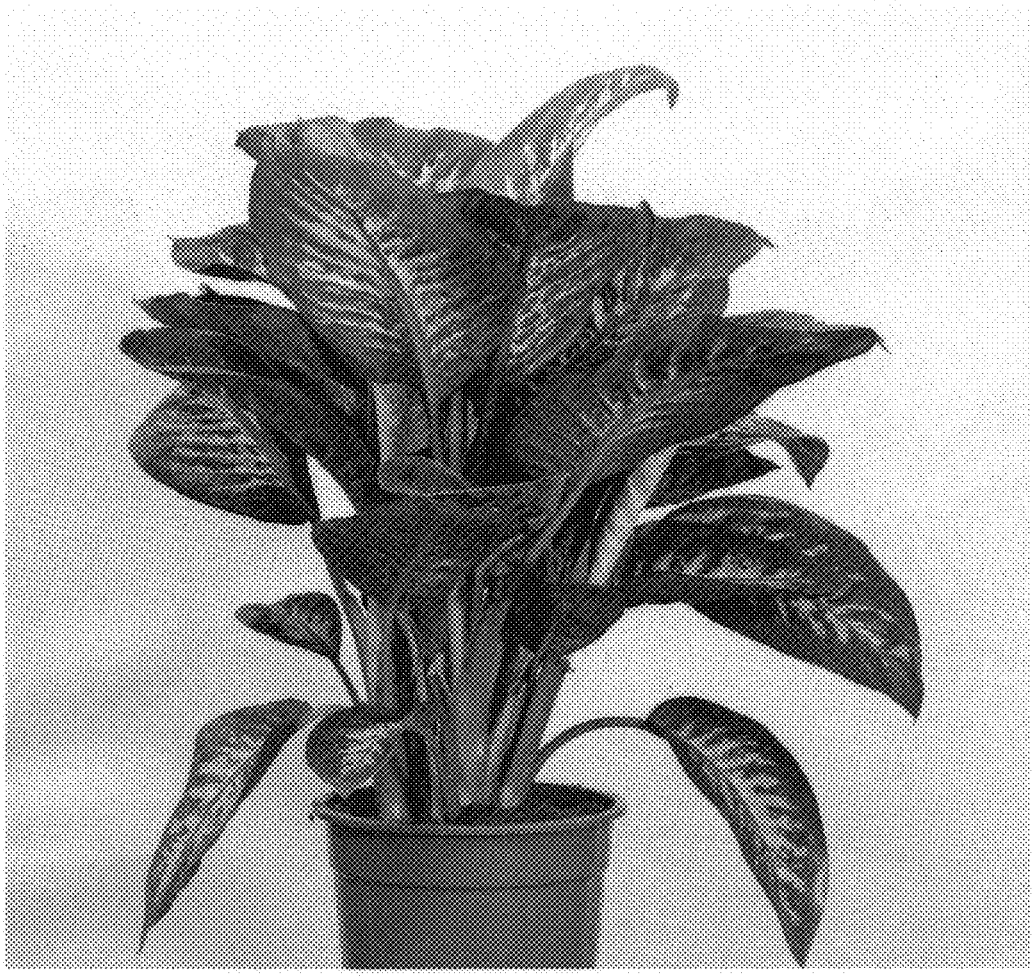
FIG. 1 shows, as nearly true as it is reasonably possible to make the same in color illustrations of this type, an exemplary 'REEVA' plant at approximately 35 weeks old, potted into a 21 cm nursery container, grown in a greenhouse in Rijsenhout, The Netherlands.
Figure 2:
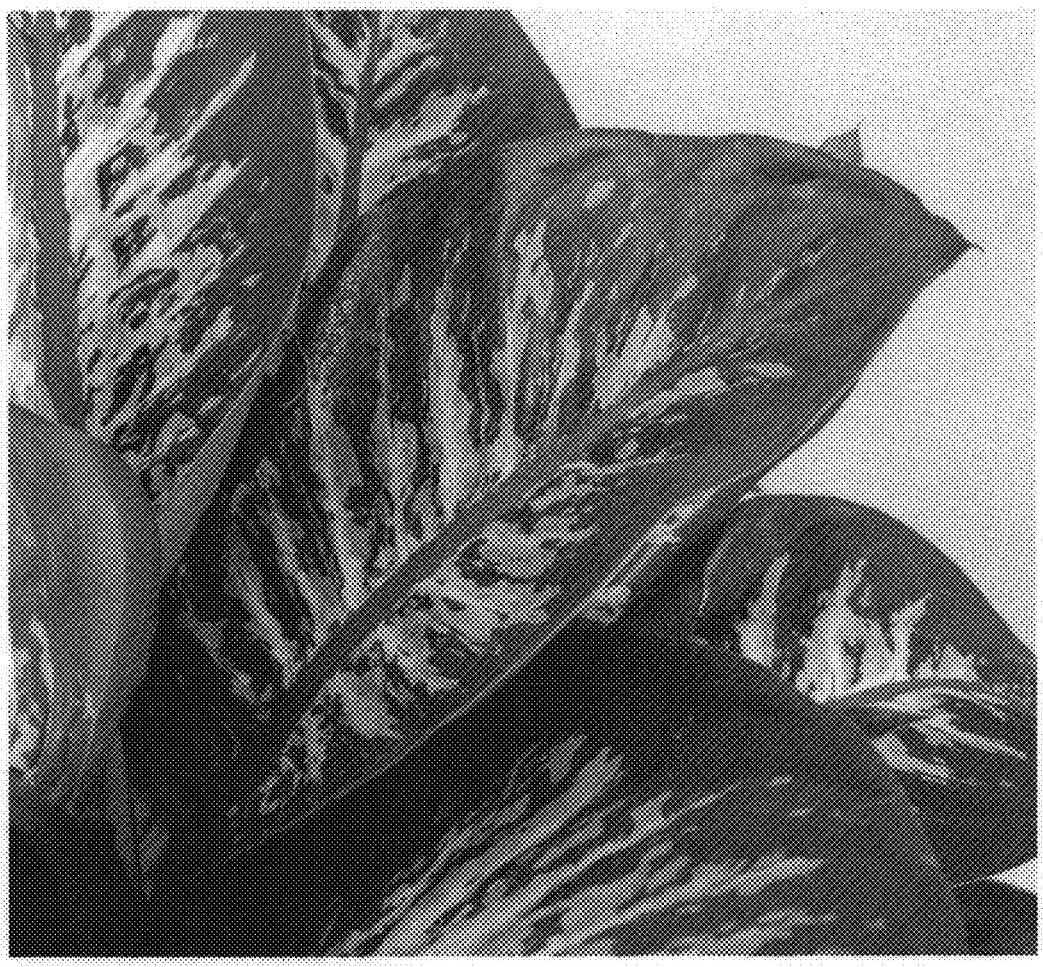
FIG. 2 shows, as nearly true as it is reasonably possible to make the same in color illustrations of this type, the typical foliage of 'REEVA'.

The following is a detailed botanical description of a new and distinct variety of *Dieffenbachia* known as 'REEVA', based upon observations of plants, approximately 35 weeks old from a rooted cutting, grown in 24 cm nursery container in a climate-controlled greenhouse in Rijsenhout, The Netherlands. Observation data was recorded in October of 2017. Plants were produced using conventional greenhouse production protocols for *Dieffenbachia* which consisted of regular 2.2 to 2.5 EC fertilizer applications and regular ebb and flow (i.e. flood bench) irrigation. No pest or disease control measures were utilized in production. Plants were produced under 50 percent shade and no photoperiodic treatments or artificial light was given to the plants.

Those skilled in the art will appreciate that certain characteristics will vary with older or, conversely, with younger plants. 'REEVA' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 edition.

A botanical description of 'REEVA' and comparisons with the parent and the most similar variety of common knowledge are provided below.

General plant description:

*Growth habit*.—Clump forming; compact upright perennial.

*Plant form*.—Obovate.

*Growth rate*.—Moderately fast growing.

*Plant vigor*.—Moderately vigorous.

*Height*.—62.5 cm.

*Width*.—66.3 cm.

*Propagation*.—Softwood stem cuttings.

*Time to initiate roots*.—Approximately 20 days to initiate roots at approximately 21 degrees Centigrade.

*Time to produce a finished plant*.—Approximately 35 weeks.

*Environmental tolerances*.—USDA Zones 10 to 12; at least tolerant of temperatures of up to 40 degrees Celsius. Moderate to high tolerance to rain inundation; low tolerance to wind.

*Pest resistance and susceptibility*.—Plants have not been observed to be susceptible or resistant to pathogens and pests common to *Dieffenbachia*.

Root system:

*General*.—Slightly fibrous and fleshy; freely branched, and moderately dense.

*Length of primary roots*.—21.0 cm.

*Diameter of primary roots*.—0.6 cm.

*Color*.—Yellow-white, nearest to a combination of RHS 158C and 158D.

*Texture*.—Smooth.

Stems:

*Branching habit*.—Main shoots arise from the soil and are freely branched with lateral branches.

*Number of main shoots per plant*.—7.

*Number of lateral branches per plant*.—3.

*Appearance; cross-section*.—Rounded.

*Length of main shoots*.—10.7 cm.

*Diameter of main shoots*.—2.8 cm.

*Internode length on main shoots*.—2.6 cm.

*Aspect*.—Erect; approximately 5 degrees from vertical.

*Strength*.—Strong.

*Color, juvenile*.—Yellow-green, nearest to in between RHS 145C and 145D.

*Color, mature*.—Yellow-green, nearest to RHS 144A, and darkening to in between green, RHS 143A, to yellow-green, RHS 146A, when matured.

*Color at internodes*.—Yellow-green, nearest to RHS 144A, and darkening to in between green, RHS 143A, to yellow-green, RHS 146A, when matured.

*Texture and luster*.—Glabrous, smooth and very slightly glossy.

Foliage:

*Arrangement*.—Alternate.

*Division*.—Simple.

*Quantity of leaves per lateral branch*.—Average of 6.

*Leaf shape*.—Obovate.

*Leaf apex*.—Apiculate with an abruptly acute tip.

*Leaf base*.—Truncate.

*Aspect*.—Flat; very slightly carinate, slightly reflexed.

*Attitude*.—Upward and outward.

*Leaf length*.—Average 31.2 cm in length.

*Leaf width*.—Average 19.0 cm in width.

*Leaf margin*.—Entire; very slightly undulate.

*Texture, adaxial surface*.—Glabrous, slightly coriaceous and slightly glossy.

*Texture, abaxial surface*.—Glabrous, slightly coriaceous and slightly glossy.

*Juvenile color, adaxial surface*.—Green, nearest to a mixture of RHS 143A, 143B, 143C and 144A; areas surrounding the secondary veins are green to yellow-green, nearest to a combination of RHS 145C, 145D, and 150D.

*Juvenile color, abaxial surface*.—Nearest to in between green, RHS 143A, and yellow-green, RHS 146B; areas surrounding the secondary veins are green to yellow-green, nearest to a combination of RHS 145B, 145C, 145D and 150D.

*Mature color, adaxial surface*.—Nearest to in between yellow-green, RHS 147A, and greyed-green, RHS 189A; centrally and irregularly blotched yellow-green, nearest to a combination of RHS 144A, 144B, 145A, 145B, 145C, 145D and 150D.

*Mature color, abaxial surface*.—Nearest to in between green, RHS 137B, and yellow-green, RHS 147B; centrally and irregularly blotched yellow-green, nearest to a combination of RHS 144C, 144D, 145B and 145C.

*Venation*.—Vein pattern — Pinnate. Vein color, adaxial surface — Green, nearest to RHS 137B. Vein color, abaxial surface — Yellow-green, nearest to a mixture of RHS 145A and 145B.

*Petiole*.—Length — Approximately 18.7 cm. Diameter — Petioles are u-shaped; average width is 0.8 cm; average height is 1.0 cm. Texture and luster, adaxial surface — Glabrous, smooth, and moderately glossy. Texture and luster, abaxial surface — Glabrous, smooth and slightly glossy. Color, adaxial surface — Green, nearest to RHS 143A. Color, abaxial surface — Yellow-green, nearest to RHS 147B. Strength — Strong. Geniculum — None present. Petiole wings — Length — Approximately 14.4 cm. Width — Approximately 1.1 cm. Color, outer surface — Green, nearest to RHS 143A. Color, abaxial surface — Yellow-green, nearest to in between RHS 145A and 147D.

Inflorescence: No flowers observed to date.

Flower bud: No flowers observed to date.

Flower: No flowers observed to date.

Reproductive organs: No flowers observed to date.

Seed and fruit: No flowers observed to date.

Comparisons With the Parents

Plants of the new cultivar 'REEVA' differ from its parent, *Dieffenbachia amoena* 'Tropic Snow' (U.S. Plant Pat. No. 2,869), by the characteristics described in Chart 1.

CHART 1

| Comparison Between 'Reeva' and 'Tropic Snow' | | |
|---|---|---|
| Characteristic | 'REEVA' | 'Tropic Snow' |
| Quantity of main shoots. | More shoots. | Less shoots. |
| Growth habit. | More compact. | Less compact. |

Comparisons With the Most Similar Variety of Common Knowledge

Plants of the new cultivar 'REEVA' may be distinguished from the commercial variety *Dieffenbachia* 'Morlix' (not patented in the United States; Netherlands and French PBR grants terminated) by the combination of characteristics described in Chart 2.

CHART 2

| Comparison Between 'Reeva' and 'Morlix' | | |
|---|---|---|
| Characteristic | 'REEVA' | 'Morlix' |
| Rate of growth. | Faster growing. | Slower growing. |
| Quantity of main shoots. | More shoots. | Less shoots. |
| Growth habit. | More compact; more freely branching and more densely foliaged. | Less compact; less freely branched and less densely foliaged. |

That which is claimed is:

1. A new and distinct variety of *Dieffenbachia* plant named 'REEVA', substantially as described and illustrated herein.

* * * * *